(12) United States Patent
Distefano

(10) Patent No.: US 10,792,143 B2
(45) Date of Patent: Oct. 6, 2020

(54) SNAP LOCK PACKAGING

(71) Applicant: Howmedica Osteonics Corp., Mahwah, NJ (US)

(72) Inventor: Nicole Distefano, Denville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 66 days.

(21) Appl. No.: 15/964,699

(22) Filed: Apr. 27, 2018

(65) Prior Publication Data

US 2018/0311027 A1    Nov. 1, 2018

Related U.S. Application Data

(60) Provisional application No. 62/491,419, filed on Apr. 28, 2017.

(51) Int. Cl.
| | |
|---|---|
| *A61B 50/30* | (2016.01) |
| *A61F 2/00* | (2006.01) |
| *A61B 50/20* | (2016.01) |
| *A61B 17/86* | (2006.01) |
| *A61B 50/00* | (2016.01) |
| *B65D 85/00* | (2006.01) |

(52) U.S. Cl.
CPC .......... *A61F 2/0095* (2013.01); *A61B 17/865* (2013.01); *A61B 50/20* (2016.02); *A61B 50/30* (2016.02); *A61B 2050/0083* (2016.02); *B65D 85/00* (2013.01)

(58) Field of Classification Search
CPC ....... A61F 2/0095; A61B 50/20; A61B 50/30; A61B 17/865; A61B 2050/0083; B25H 3/003; B65D 25/10

USPC .......................................... 206/363, 372, 438
See application file for complete search history.

(56) References Cited

U.S. PATENT DOCUMENTS

| | | | |
|---|---|---|---|
| 2,846,806 | A | 8/1958 | Gaines |
| 3,376,973 | A | 4/1968 | Granowitz et al. |
| 3,444,994 | A | 5/1969 | Kaepernick |

(Continued)

FOREIGN PATENT DOCUMENTS

| | | |
|---|---|---|
| WO | 03079918 A1 | 10/2003 |
| WO | 2005016183 A1 | 2/2005 |

OTHER PUBLICATIONS

The Partial European Search Report for EP Application No. 16203879.8 dated Apr. 20, 2017.

*Primary Examiner* — Steven A. Reynolds
(74) *Attorney, Agent, or Firm* — Lerner, David, Littenberg, Krumholz & Mentlik, LLP

(57) ABSTRACT

The present invention relates to packages and methods of using packages that provide a sterile enclosure for an implant so that the implant can be transported and retrieved without being contaminated. In one embodiment, the package includes an insert with an implant disposed therein and a tray. The insert includes a first engagement feature and the tray includes a second engagement feature corresponding to the first engagement feature. The insert is sized to fit within and engage with the tray through engagement of the first and second engagement features, where in a first position the implant is secured within the package and in a second position, the implant is retrievable from the insert. The insert moves relative to the tray between the first and positions, but remains secured to it in both positions.

14 Claims, 8 Drawing Sheets

(56) References Cited

U.S. PATENT DOCUMENTS

| | | |
|---|---|---|
| 3,554,429 A | 1/1971 | Cohen |
| 3,613,879 A | 10/1971 | Kemble |
| 3,616,898 A | 11/1971 | Massie |
| 3,759,376 A | 9/1973 | Lisowski |
| 3,972,418 A | 8/1976 | Schuler et al. |
| 4,111,302 A | 9/1978 | Roth |
| 4,142,632 A | 3/1979 | Sandel |
| 4,324,331 A | 4/1982 | Ignasiak |
| 4,482,053 A | 11/1984 | Alpern et al. |
| 4,511,035 A | 4/1985 | Alpern |
| 4,602,715 A | 7/1986 | Sarver et al. |
| 4,708,241 A | 11/1987 | Black |
| 4,782,942 A | 11/1988 | Ashley et al. |
| 4,842,141 A | 6/1989 | Segal |
| 4,850,477 A | 7/1989 | Gelardi et al. |
| 4,903,827 A | 2/1990 | Phelps et al. |
| 4,945,710 A | 8/1990 | Hustad |
| 4,978,510 A | 12/1990 | Smith |
| 4,986,414 A | 1/1991 | Ashley et al. |
| D315,868 S | 4/1991 | Gelardi et al. |
| 5,076,431 A | 12/1991 | Thompson |
| D326,409 S | 5/1992 | Krueger et al. |
| 5,123,528 A | 6/1992 | Brown et al. |
| 5,129,511 A | 7/1992 | Brown et al. |
| 5,133,454 A | 7/1992 | Hammer |
| 5,176,258 A | 1/1993 | Antal |
| 5,246,109 A | 9/1993 | Markle et al. |
| 5,277,299 A | 1/1994 | Holzwarth et al. |
| 5,341,934 A | 8/1994 | Hsu |
| 5,353,922 A | 10/1994 | Sinn |
| 5,368,160 A | 11/1994 | Leuschen et al. |
| 5,379,895 A | 1/1995 | Foslien |
| 5,388,701 A | 2/1995 | Ridgeway |
| 5,392,903 A | 2/1995 | Sinn |
| 5,392,917 A | 2/1995 | Alpern et al. |
| 5,405,000 A | 4/1995 | Hagedon et al. |
| 5,405,005 A | 4/1995 | White |
| 5,441,150 A | 8/1995 | Ma |
| 5,447,234 A | 9/1995 | Faulstick et al. |
| 5,497,601 A | 3/1996 | Gonzalez |
| 5,562,208 A * | 10/1996 | Hasler .................. B25F 1/00 |
| | | 206/373 |
| 5,590,778 A | 1/1997 | Dutchik |
| 5,669,501 A | 9/1997 | Hissong et al. |
| 5,685,429 A | 11/1997 | Myers |
| 5,690,222 A | 11/1997 | Peters |
| 5,772,025 A | 6/1998 | Chen et al. |
| 6,182,480 B1 | 2/2001 | Kim |
| 6,622,864 B1 | 9/2003 | Debbs et al. |
| 6,783,004 B1 | 8/2004 | Rinner |
| 6,814,236 B2 | 11/2004 | Roshdy |
| 6,827,212 B2 | 12/2004 | Reaux |
| 6,830,149 B2 | 12/2004 | Merboth et al. |
| 6,843,374 B1 | 1/2005 | Li et al. |
| 6,889,839 B1 | 5/2005 | Rosten et al. |
| 6,915,901 B2 | 7/2005 | Feinberg et al. |
| 6,994,213 B2 | 2/2006 | Giard, Jr. et al. |
| 7,066,329 B2 | 6/2006 | Riley |
| 7,270,235 B2 * | 9/2007 | Chen .................. B25H 3/003 |
| | | 206/349 |
| 7,475,776 B2 | 1/2009 | Detruit et al. |
| 7,650,991 B2 | 1/2010 | Hester et al. |
| 7,770,728 B2 | 8/2010 | Kærn |
| 7,832,560 B2 | 11/2010 | Tilton |
| 7,931,143 B1 * | 4/2011 | Lin .................. B25H 3/021 |
| | | 206/373 |
| 8,006,839 B2 | 8/2011 | Hafner |
| 8,079,468 B2 | 12/2011 | Pleil et al. |
| 8,096,420 B2 | 1/2012 | Marhsall et al. |
| 8,112,973 B2 | 2/2012 | Fischer et al. |
| 8,113,348 B2 | 2/2012 | Foster |
| 8,177,066 B2 | 5/2012 | Tilton |
| 8,240,468 B2 | 8/2012 | Wilkinson et al. |
| 8,403,941 B2 | 3/2013 | Peterson et al. |
| 8,413,811 B1 | 4/2013 | Arendt |
| 8,496,690 B2 | 7/2013 | Sixto et al. |
| 8,511,473 B1 | 8/2013 | Bontrager et al. |
| 8,518,341 B2 | 8/2013 | Friderich et al. |
| 8,584,853 B2 | 11/2013 | Knight et al. |
| 8,701,890 B2 | 4/2014 | Bertazzoni et al. |
| 8,701,891 B2 | 4/2014 | Bontrager et al. |
| D712,279 S | 9/2014 | Akana et al. |
| 9,017,851 B2 | 4/2015 | Felder et al. |
| 9,095,848 B2 | 8/2015 | Carrel et al. |
| 9,101,349 B2 | 8/2015 | Knight et al. |
| D752,430 S | 3/2016 | Stevenson et al. |
| 9,687,300 B2 | 6/2017 | Hartfelder et al. |
| 9,707,039 B2 | 7/2017 | Grabowski et al. |
| 10,086,131 B2 | 10/2018 | Okihara |
| 10,245,025 B2 | 4/2019 | Prikril et al. |
| 2002/0112981 A1 | 8/2002 | Cooper et al. |
| 2002/0125158 A1 | 9/2002 | High et al. |
| 2003/0121810 A1 | 7/2003 | Roshdy |
| 2005/0017059 A1 | 1/2005 | Salani et al. |
| 2005/0033430 A1 | 2/2005 | Powers et al. |
| 2005/0173278 A1 | 8/2005 | Caron |
| 2005/0241974 A1 * | 11/2005 | Chen .................. B25H 3/003 |
| | | 206/379 |
| 2006/0243616 A1 | 11/2006 | Caron |
| 2007/0034538 A1 | 2/2007 | Landis |
| 2008/0029419 A1 | 2/2008 | Appelbaum |
| 2008/0190794 A1 | 8/2008 | Farrar et al. |
| 2008/0283443 A1 | 11/2008 | Green |
| 2009/0266728 A1 | 10/2009 | Turner et al. |
| 2011/0113437 A1 | 5/2011 | Day |
| 2011/0186456 A1 | 8/2011 | Bertazzoni et al. |
| 2011/0288596 A1 | 11/2011 | Brand et al. |
| 2012/0256748 A1 | 10/2012 | Russell et al. |
| 2013/0233736 A1 | 9/2013 | Hess et al. |
| 2014/0215976 A1 | 8/2014 | Maasarani |
| 2014/0360900 A1 | 12/2014 | Mizuoka et al. |
| 2015/0021221 A1 | 1/2015 | Hendrickson et al. |
| 2016/0101891 A1 | 4/2016 | Bailey et al. |
| 2016/0262905 A1 | 9/2016 | Prado et al. |
| 2016/0304260 A1 | 10/2016 | Ahn |
| 2017/0056122 A1 | 3/2017 | Ramsey |
| 2018/0263721 A1 | 9/2018 | Volk et al. |

* cited by examiner

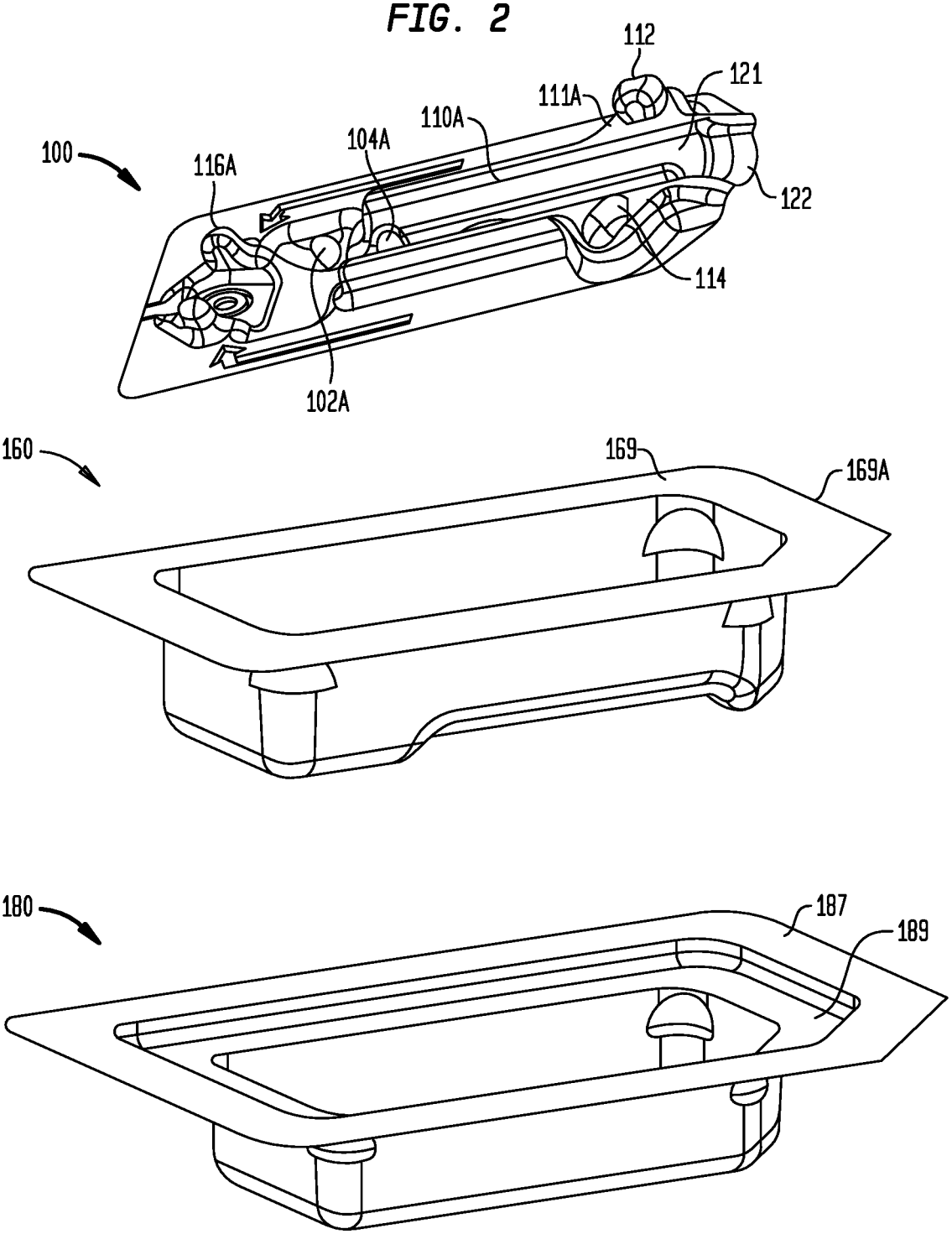

SNAP LOCK PACKAGING

CROSS-REFERENCE TO RELATED APPLICATIONS

The present application claims the benefit of U.S. Provisional Patent Application No. 62/491,419, filed on Apr. 28, 2017, the disclosure of which is incorporated by reference herein in its entirety.

BACKGROUND OF THE INVENTION

Packaging for surgical implants exists in a variety of forms. A number of package designs include an outer package with an implant inside. The implant is sometimes affixed to a smaller package within the outer package. Although past efforts have sought improvement in package design tailored for use with implants, the art has failed to develop an improved package design that maintains the sterility of implants during deposit, storage and retrieval. Deposit and retrieval are of particular significance because without a sterility preserving approach for the deposit and retrieval of an implant, any sterility preserved during storage could be squandered when the implant is first placed into the package or when it is retrieved at a later time for use. For example, it may be necessary for a surgeon to retrieve the implant from the package by hand, or contact with the implant may otherwise occur due to difficulty manipulating the package so that the implant can be retrieved. It is also frequently seen that manipulation of the package results in the implant being dropped or otherwise exposed to non-sterile environments. In addition to the challenge of limiting contamination, the implant must be physically secured in place within the package for storage and transport.

Thus, there is a need for improved packaging and methods of using packaging that can safely secure an implant and can also maintain the sterility of the implant during transfer of the implant into and from the package, as well as while the implant is stored in the package.

BRIEF SUMMARY OF THE INVENTION

One aspect of the present disclosure may generally relate to a packaging assembly that includes an insert disposable in a tray. The insert is sized and shaped so that an implant can be stored within a cavity in the insert. The insert also includes an engagement feature shaped to correspond to and engage with an engagement feature of the tray. The insert is secured to the tray when the respective engagement features are engaged. Moreover, the insert is adjustable into at least two different positions relative to the tray while it remains secured to the tray. In both positions of the insert, at least some portion of the respective engagement features of the insert and tray remain engaged with one another.

The aforementioned engagement features provide stable securement between the insert and the tray so that the insert remains in a relatively fixed position relative to the tray in both first and second positions. Manipulation of the insert through application of force on a first end moves it from the first to second position while application of force on a second end moves it from the second position back to the first position. The physical features of the packaging assembly are such that the implant is retrievable when the insert is in one of the first and second positions but not retrievable in the other of the first and second positions.

In one embodiment, the package includes a tray and an insert. The tray includes a recessed portion with a bottom surface, the bottom surface including a first engagement feature. The insert is sized to fit within the recessed portion of the tray and has a second engagement feature. Further, the insert is adapted to support disposal of an implant therein. The insert is releasably secured to the tray when the first engagement feature is engaged with the second engagement feature. Additionally, the insert is moveable while releasably secured to the tray such that the implant, when disposed in the insert, is inaccessible when the insert is in a first position and is accessible when the insert is in a second position. A quantity of engagement features engaged with one another in the first position is different than in the second position.

In other embodiments, the first and second engagement features are protrusions or indents. In yet another embodiment, the engagement between the second engagement feature of the insert and the first engagement feature of the tray is sufficient to stabilize the insert in the second position.

In other embodiments, the package includes a third engagement feature on the bottom surface of the tray such that the first engagement feature is located at a first location on a length of the tray and the third engagement feature is located at a second location on the length of the tray. In this arrangement, the first location is different from the second location. Complementing the third engagement feature on the tray is a fourth engagement feature on the insert. These engagement features are positioned and engageable with one another so that the implant, when disposed in the insert, is (1) inaccessible when the third engagement feature is engaged with the fourth engagement feature and is (2) accessible when the third engagement feature is disengaged with the fourth engagement feature. In a variant, the third engagement feature has a shape different than a shape of the first engagement feature. In another variant, the first engagement feature is one of an indent or protrusion and the third engagement feature is the other of the indent or protrusion. In still another variant, the third engagement feature is at a first distance from the bottom surface and the first engagement feature is at a second distance from the bottom surface, the first distance different than the second distance.

In other embodiments, the package includes a third engagement feature on the bottom surface of the tray positioned across a longitudinal centerline of the tray opposite the first engagement feature so that a distance of each of the first and third engagement features from the longitudinal centerline of the tray is the same. In this arrangement, the third engagement feature corresponds to a fourth engagement feature of the insert. In a variant, the tray further comprises a fifth and a sixth engagement feature separated by a second distance different than the distance between the first and third engagement features of the tray.

In one embodiment, a package includes a tray with two engagement features and an insert with two engagement features corresponding to the two engagement features of the tray. The engagement features correspond in a manner such that the insert is engageable with the tray and the insert is movable with respect to the tray while engaged thereto. The two engagement features of the insert, when engaged with the tray, are positioned so that the insert pivots about an axis passing through each of the two engagement features, the insert pivoting about the axis from a first position to a second position. The insert is adapted to secure an implant therein, the implant inaccessible in the first position and accessible in the second position.

In other embodiments, a surface of the insert is parallel to a surface of the tray in the first position and at an angle with respect to the surface of the tray in the second position. In still other embodiments, the implant, when disposed in the insert engaged with the tray in the second position, is coincident with a second axis that only crosses the tray on one side of the insert. In a variant, the second axis is at an angle between 10 degrees and 20 degrees relative to a bottom surface of a recessed portion of the tray. In other embodiments, the insert includes a cavity shaped to store the implant therein and to hold the implant in place when the insert is in the second position.

In another aspect, the present disclosure relates to a method of positioning an insert in a tray. One embodiment of the method includes a step of applying pressure onto one end of the insert disposed in the tray so that the insert moves from a first position where a plane through a body of the insert is approximately parallel to a plane through a body of the tray to a second position where the plane through the body of the insert is not parallel to the plane through the body of the tray. In this method, the insert is releasably secured to the tray in the first and second positions. Further, the insert remains in the first or second position through engagement between the insert and the tray once the insert is moved into the first or the second position.

In other embodiments, the method includes an additional step of placing the insert into the tray prior to the applying pressure step such that a first engagement feature of the insert engages with a second engagement feature of the tray and the insert is in a first position. In a variant, the method further includes placing an implant into a cavity in the insert prior to placing the insert into the tray. In further variants, placing the insert into the first position with respect to the tray secures the implant within the cavity of the insert. In another variant, the method includes removing the implant from the insert when the insert is in the second position.

In other embodiments, movement of the insert from the first position to the second position disengages a first engagement feature of the insert from a second engagement feature of the tray.

BRIEF DESCRIPTION OF THE DRAWINGS

The present invention will be better understood on reading the following detailed description of non-limiting embodiments thereof, and on examining the accompanying drawings, in which:

FIG. 2 is an exploded view of the packaging assembly of FIG. 1 including an insert component representing a part of an insert shown in FIG. 1 in place of the insert shown in FIG. 1.

DETAILED DESCRIPTION

The present invention is directed to a snap lock packaging assembly for use in safely storing and accessing medical implants or parts, such as screws. Specifically, the present invention provides two or more components, one insertable into and securable with the other so that an implant stored in the insertable component is inaccessible in at least one position and accessible in another position when the components are engaged with one another. In this manner, the implant can be transported without contact by any non-sterile surface or object, including human hands. In addition, a position of the inserted component can be adjusted without contacting the implant. Thus, the assembly provides for storage, transport and access to implants while minimizing the risk of contamination.

Figure 1:
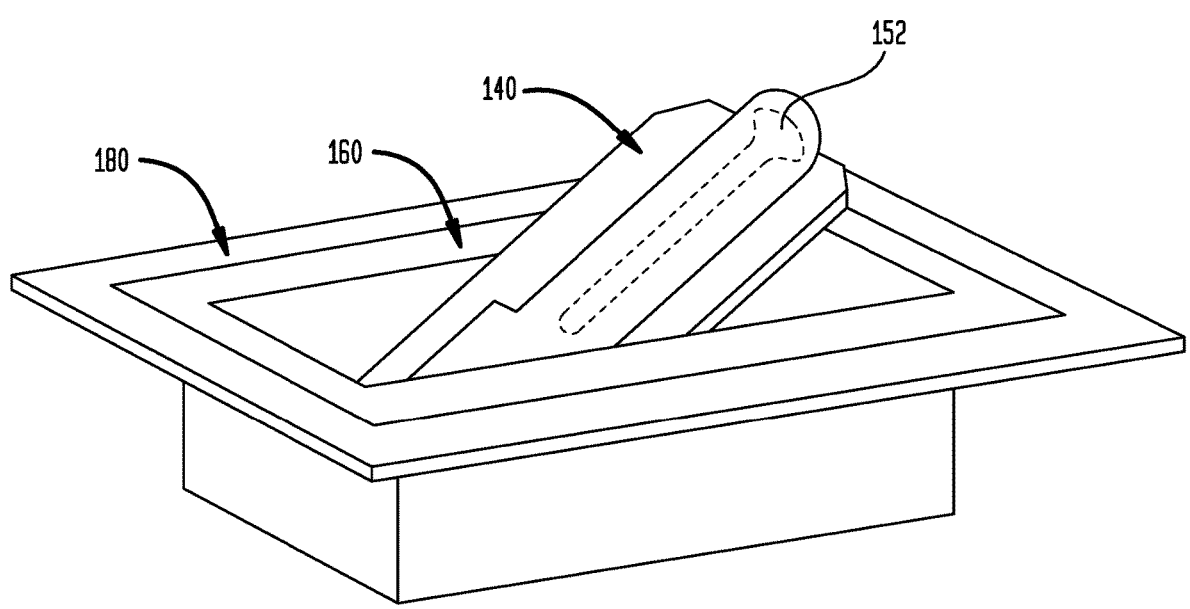
FIG. 1 is a perspective view of a packaging assembly according to one embodiment of the present invention.

Turning now to the various embodiments of the invention, FIG. 1 depicts one embodiment of a packaging assembly including an insert 140, an inner tray 160 and an outer tray 180. Insert 140 is sized to fit within and is releasably securable to inner tray 160 while inner tray 160 is sized to fit within outer tray 180. Details of the structure for securement between the components are described below. As shown in FIG. 2, inner tray 160 includes an outer rim surface 169 sized to correspond to surface 189 of outer tray 180 so that an outer edge 169A of inner tray 160 is flush with a surface of outer tray 180 when inner tray 160 is disposed therein.

Figure 3A:
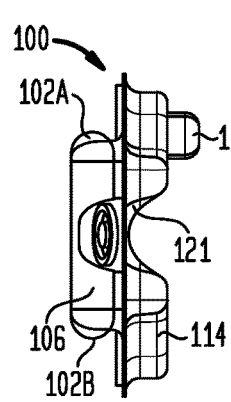
FIGS. 3A-3C are plan and side views of the insert component of FIG. 2.
Figure 3B:
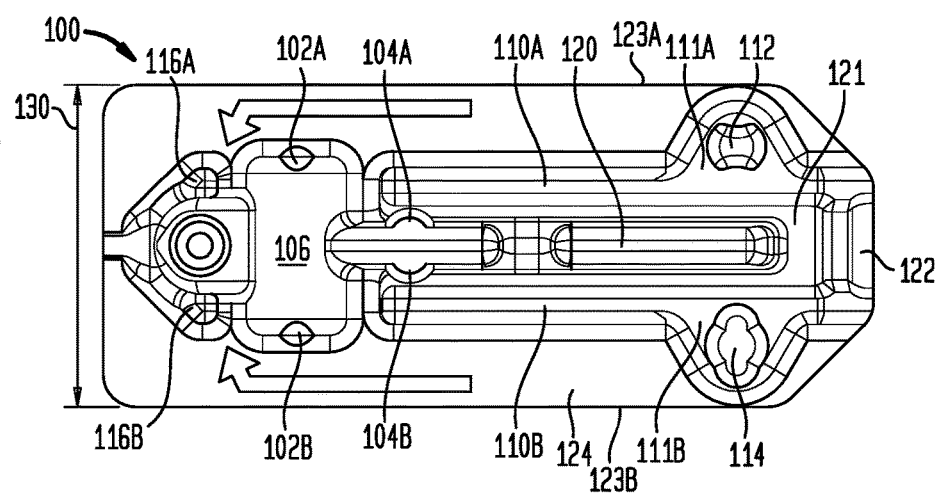
Figure 3C:
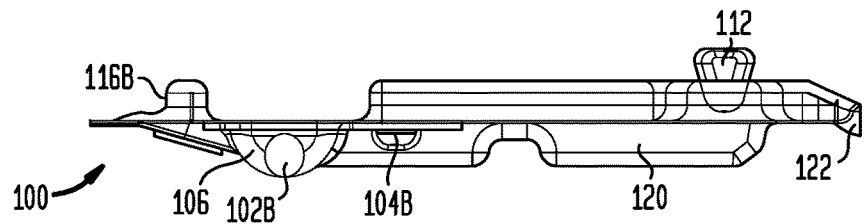

As mentioned above, insert 140 is shaped for insertion within and securement to inner tray 160. Insert 140 as illustrated in FIG. 1 includes two insert components (e.g., FIGS. 3A-3C) attached together generally in the manner depicted in FIG. 6 and described in greater detail below. The detailed structural features of each insert component 100 are as follows. A first width 130 (see FIG. 3B) of the insert component is smaller than a second width 175 (see FIG. 4B) of a volume 168 of inner tray 160, so that insert 140 fits within inner tray 160. FIGS. 3A-3C illustrate several views of each insert component 100. Insert component 100 includes a concave recess 106 wholly between edges 123A and 123B. Extending laterally from an end face of recess 106 toward edge 123A on one side of the recess and edge 123B on the other side are engagement features in the form of protrusions 102A, 102B, respectively. An outward projection of such protrusions is best shown in FIG. 3A.

Insert component 100 also includes a channel surface 121 extending from a location adjacent to concave recess 106 to an end of insert component 100 where surface 121 becomes a tapered channel surface 122. At an outer bound of a width of channel surface 121 are ridges 110A, 110B extending parallel to channel surface 121 and standing proud of channel surface 121 in a direction distal to surface 124. Proximal to tapered channel surface 122, ridges 110A, 110B widen into bulges 111A, 111B. From surface of bulge 111A extends an insert interconnection protrusion 112 and depressed from surface of bulge 111B is insert interconnection indent 114. Returning to channel surface 121, within the width of channel surface 121 lies depression 120, best shown in FIGS. 3B and 3C. Depression 120 extends approximately contiguously with channel surface 121. In particular, depression extends from within concave recess 106 at a first end to a location within channel surface 121 at a second end, as best shown in FIG. 3B. Proximal to concave recess 106, walls of depression 120 include mirrored engagement features in the form of outward facing protrusions 104A, 104B that protrude so that the wall of the depression is indented and thus wider at protrusions 104A, 104B (FIG. 2). In this manner, from a surface (not shown) of insert component 100 opposite surface 124, protrusions 104A, 104B are protruding outward, or laterally, relative to a length of channel surface 121, toward edges 123A, 123B.

In summary, channel surface 121 is bound by ridges 110A, 110B and extends from concave recess 106 to an end of insert component 100 where it expands in a conical fashion as tapered conical surface 122. Insert component 100 also includes supplemental protrusions 116A, 116B extending perpendicularly from surface 124 and located adjacent to concave recess 106 on a side of concave recess 106 opposite channel surface 121.

Figure 6:
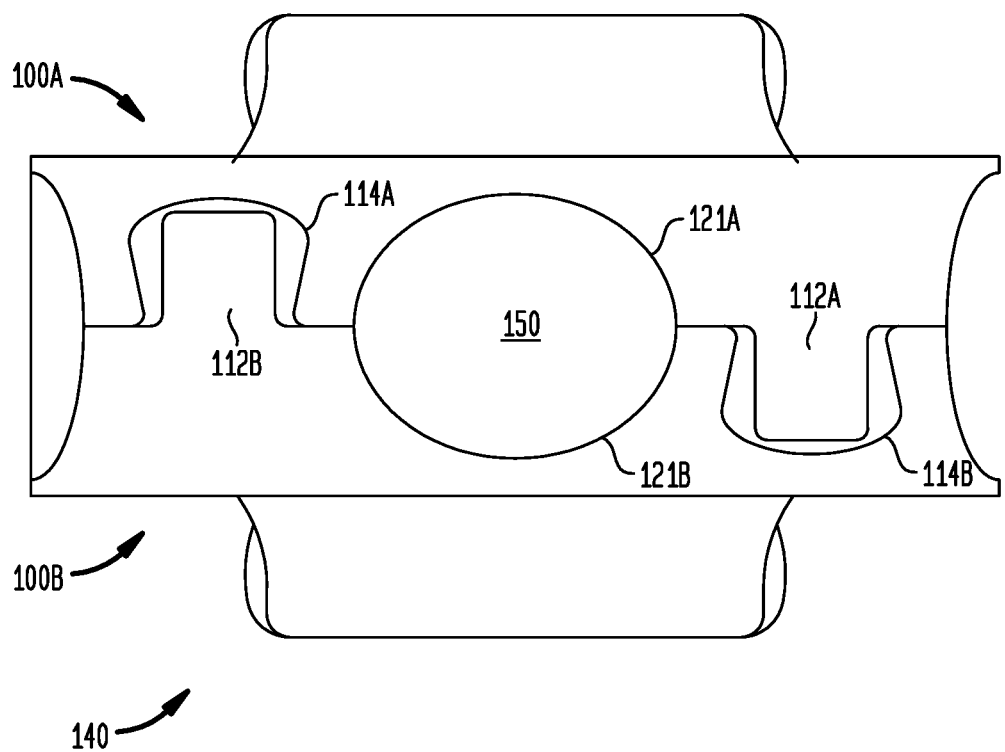
FIG. 6 is a sectional view of the insert including two of the insert components of FIG. 2.

As mentioned above, two insert components 100 as described are combined to form insert 140. In FIG. 6, the two insert components constituting insert 140 are referred to as insert component 100-A and 100-B, respectively. Securement between each insert component can be accomplished through interconnection of respective surface features on each insert component 100-A, 100-B. In this manner, insert interconnection protrusion 112 of one insert component will interconnect with insert interconnection indent 114 of the other insert component. For example, insert interconnection protrusion 112-A of upper insert component 100-A interconnects with insert interconnection indent 114-B of lower insert component 100-B. Cavity 150 is formed in part by channel surface 121-A of upper insert component 100-A and in part by channel surface 121-B of lower insert component 100-B and is shaped and sized so that an implant, such as a screw (not shown), can be disposed and stored therein. A conically tapering portion of cavity 150 at an insertion end of insert 140 provides space for the head of a screw or other implant and also holds the implant in place at a location where cavity 150 narrows to a diameter smaller than that of the implant head disposed in insert 140. It is contemplated that each insert component may be identical to the other or that each insert component may be different from the other in certain respects. In either configuration, each insert component complements the other. In this manner, one insert component is combinable with another insert component to form an insert.

In a variant of this embodiment, a single insert component 100 is used in place of insert 140 for the packaging assembly. The single insert component 100 can perform the same functions as insert 140 as described herein. It is to be understood that the specific structures shown and discussed above in connection with the insert may vary depending upon different factors, including the type of implant to be held. Additionally, other interconnection structures between different insert parts can be employed in accordance with the present invention.

Figure 4A:
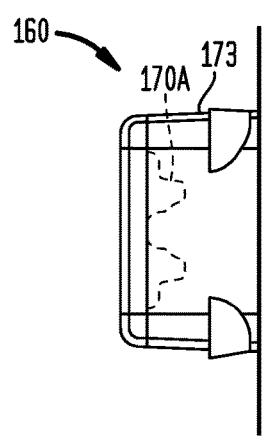
FIGS. 4A-4C are plan and side views of the inner tray of FIG. 2.
Figure 4B:
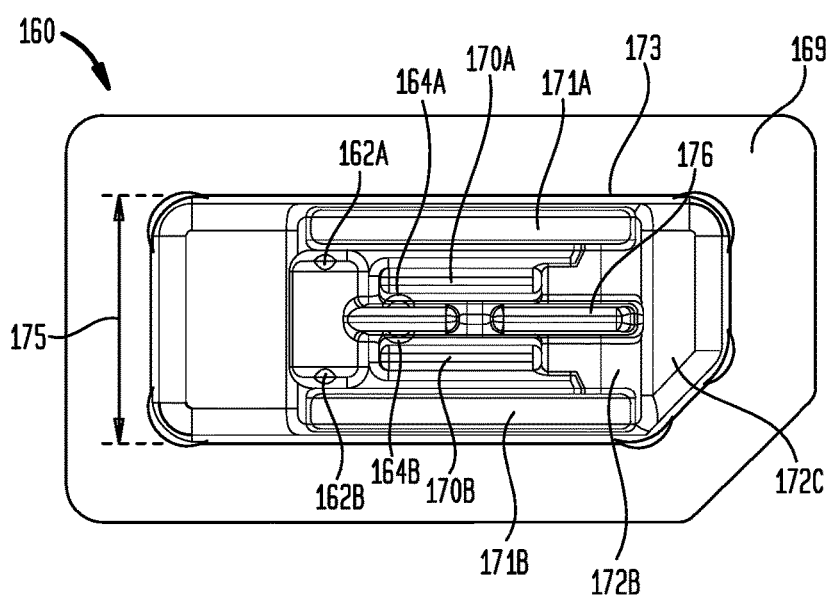
Figure 4C:
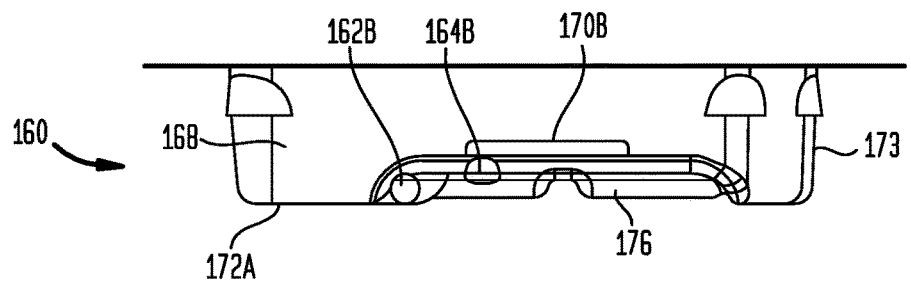

Inner tray 160 is best shown in FIGS. 4A-4C and includes volume 168 sized to accommodate disposal of insert component 100 or insert 140 therein. Volume 168, as described herein, is also referred to as a recessed portion of the inner tray. Inner tray 160 includes an outer rim surface 169 surrounding volume 168. Outer rim surface 169 as depicted is of a generally uniform thickness. Nonetheless, it is contemplated that outer rim surface 169 can include a varying width and/or thickness as a matter of design choice. The outer rim surface includes an inner edge at inner perimeter 173. The shape of inner perimeter 173 as shown is generally rectangular with a chamfer at one corner, and is of similar dimensions to the outer edge of insert component 100.

Volume 168 is generally defined by inner perimeter 173 and bottom surfaces 172A, 172B and 172C of inner tray 160. Volume 168 is further defined by interruptions in bottom surfaces 172A, 172B, and 172C including, among others, concave recess 166, tray outer ridges 171A, 171B, tray inner ridges 170A, 170B, and depression 176. In a manner similar to insert component 100, concave recess 166 exists in an interior location within inner tray 160. Depression 176 extends from concave recess 166 to a second location abutting bottom surface 172C. A width of depression 176 is defined by a space between tray inner ridges 170A, 170B, which extend contiguously with depression 176 over part of its length. Width and length dimensions of depression 176 and tray inner ridges 170A, 170B match and otherwise correspond to depression 120 and ridges 110A, 110B of insert component 100, so that the insert fits securely within inner tray 160. Further, tray inner ridges 170A, 170B include opposing engagement features in the form of indents 164A, 164B, as shown in FIG. 4B. Indents 164A, 164B are indented relative to surfaces of depression 176 making depression 176 slightly wider at the indent location. Indents 164A, 164B are sized and positioned to accept protrusions 104A, 104B of insert component 100. In this manner, indents 164A, 164B are engageable with protrusions 104A, 104B. Similarly, concave recess 166 is sized to accept and receive concave recess 106. Concave recess 166 includes engagement features in the form of indents 162A, 162B with surfaces indented relative to a surface of concave recess 166. Indents 162A, 162B are sized and positioned to accept protrusions 102A, 102B of insert component 100. In this manner, indents 162A, 162B are engageable with protrusions 102A, 102B.

While depression 176 is recessed relative to bottom surface 172B of inner tray 160, it is recessed from a surface elevated relative to bottom surfaces 172A, 172C and therefore is not deeper than the deepest bottom surface. This is visible through FIGS. 4B and 4C. Tray inner ridges 170A, 170B stand proud of bottom surface 172B of inner tray 160 and have a height greater than tray outer ridges 171A, 171B, which in turn are elevated relative to bottom surfaces 172A, 172C of inner tray (FIGS. 4A, 4C). A length of tray outer ridges 171A, 171B is approximately the length of concave recess 166 and depression 176 combined, as shown in FIG. 4B. As described in greater detail in the method, insert component 100 or insert 140 is releasably securable with inner tray 160 in one position when only two indents 162A, 162B are engaged with only two protrusions 102A, 102B, or in another position when all four indents, 162A, 162B, 164A, 164B are engaged with all four protrusions 102A, 102B, 104A, 104B. These possibilities for engagement are based on the embodiment as shown (also shown for the method in FIGS. 7A and 7B). It is contemplated that the insert and inner tray can include a wide range of engagement feature combinations, which are described in greater detail below, and thus the possibilities for engagement can vary as a function of the quantity and position of the engagement features in the applicable packaging. The structures of the insert and inner tray include the additional physical attribute that the insert remains releasably secured in its position in either of the above described positions without external assistance. In this manner, no external assistance is necessary to hold the insert in place, no matter the insert position. Thus, for example, even in the insert position where only some engagement features are engaged, insert component 100 or insert 140 remains stable through support provided by the remaining engagement features engaged with the inner tray and without any external support, such as that which could be provided by a finger used to hold the insert up.

Figure 5A:
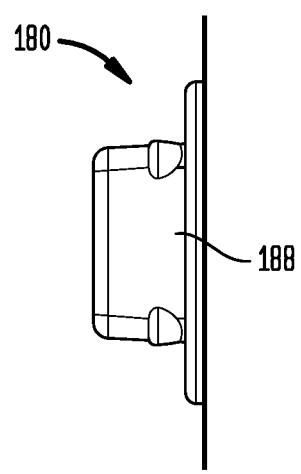
FIGS. 5A-5C are plan and side views of the outer tray of FIG. 2.
Figure 5B:
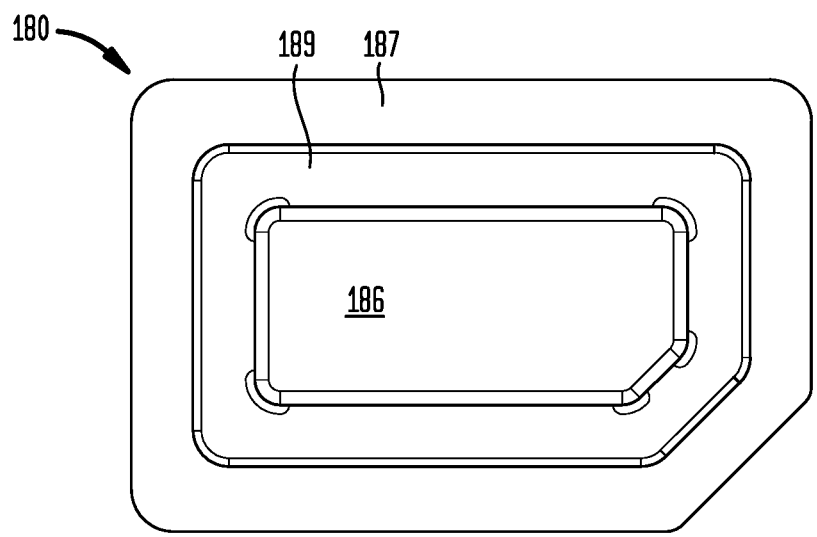
Figure 5C:
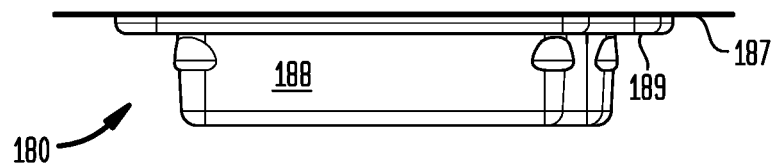

Outer tray 180 is best shown in FIGS. 5A-5C and includes an outer rim surface 187, a middle surface 189, and a volume 188 in a recessed portion. Outer tray 180 is similarly shaped to that of inner tray 160 and is of a larger size than inner tray 160 so as to accommodate disposal of inner tray 160 therein.

As depicted in FIGS. 5A-5C, and similar to FIGS. 4A-4C, volume 188 is generally rectangular though it includes three rounded corners and a chamfer at a fourth corner. Volume 188 includes a depth from a height of outer rim 187 to a bottom surface 186. Outer rim 187 defines an outer perimeter of outer tray 180 and middle surface 189 presents a slight recess or step from outer rim 187 in the direction of volume 188 and surrounds volume 188, as shown. In the depicted embodiment, outer rim surface 169 of inner tray 160 is sized to correspond with middle surface 189 when inner tray 160 is disposed in outer tray 180.

Figure 8A:
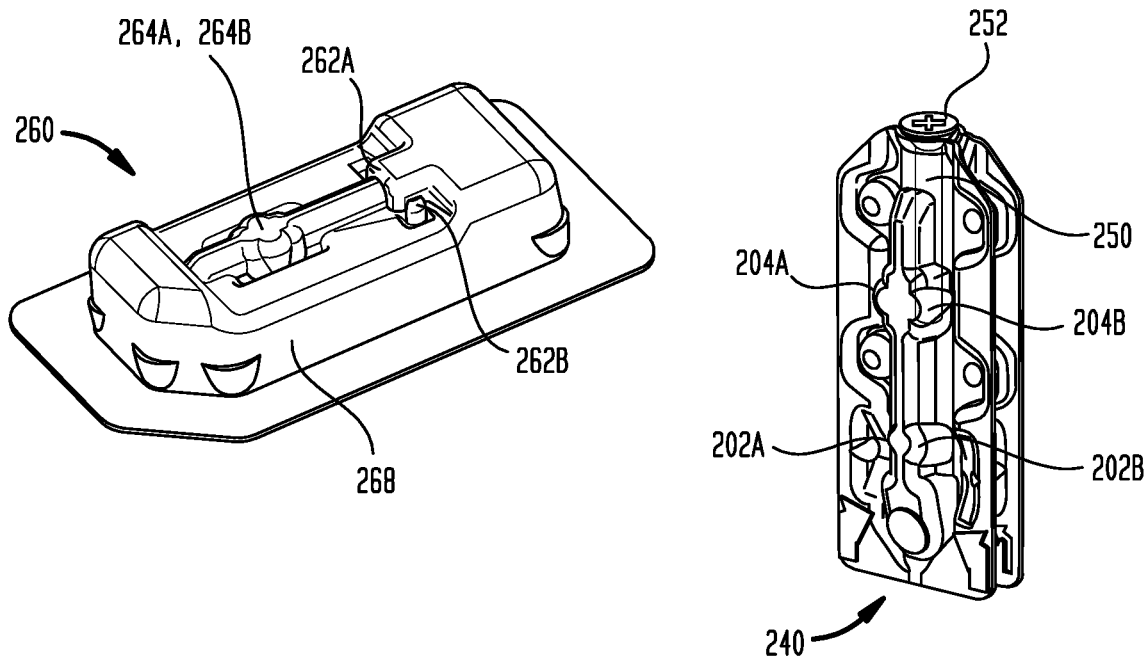
FIGS. 8A-8B are perspective views of an insert and inner tray according to another embodiment of the present invention.
Figure 8B:
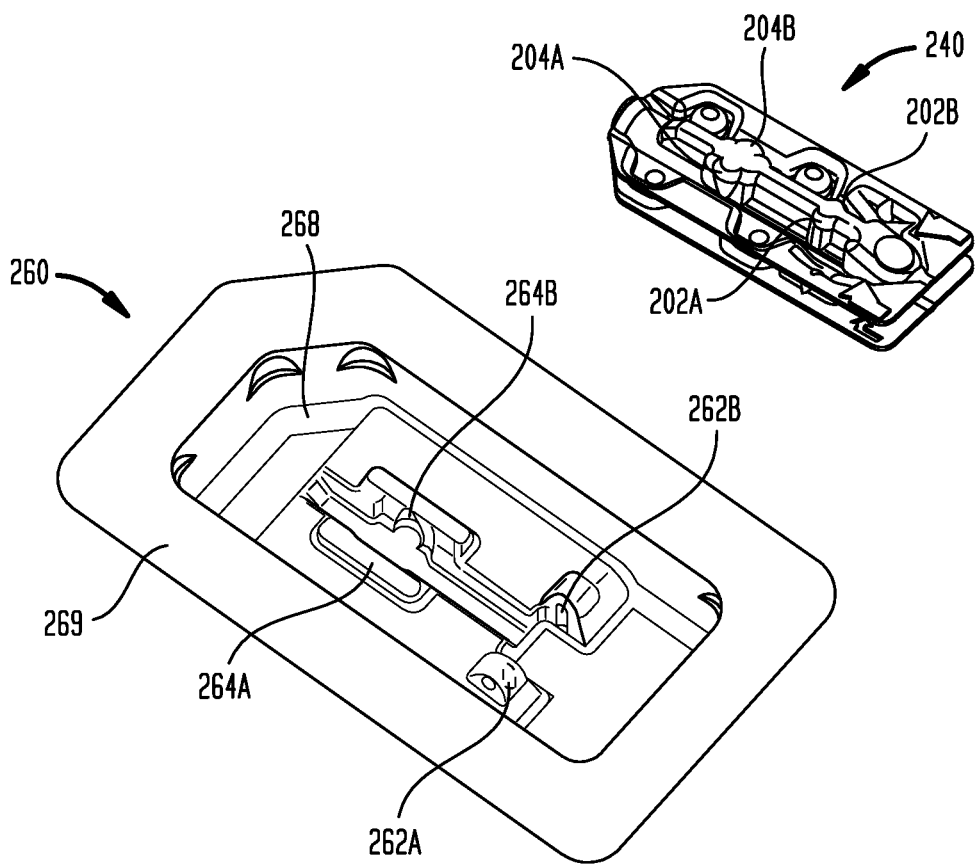

In another embodiment, a packaging assembly 290 includes an insert 240 and an inner tray 260, as shown in FIGS. 8A and 8B. Insert 240 includes a cavity 250 for disposal of an implant therein, such as implant 252. Insert 240 also includes two pairs of engagement features, 202A-B and 204A-B, each pair at different locations on a length of insert 240. Each engagement feature 202A-B, 204A-B of insert 240 is a protrusion on an outer surface of insert 240. Inner tray 260 includes an outer rim surface 269 having an inner perimeter defining the bounds of a volume 268 of a recess in inner tray 260. Volume 268 is sufficient so that insert 240 can be disposed within volume 268. Further, a surface at a bottom of volume 268 includes engagement features 262A-B and 264A-B which correspond to the engagement features of insert 240. In particular, engagement features 262A-B correspond to engagement features 202A-B and engagement features 264A-B correspond to engagement features 204A-B. As shown in FIGS. 8A and 8B, engagement features 262A-B and 264A-B are indents in the bottom surface of volume 268.

The above embodiments can be varied in many ways. For example, the insert can include a single engagement feature at a first location on its length and a single engagement feature at a second location, with corresponding features on the inner tray. In this manner, the example is distinguishable from the pairs of engagement features (e.g., 102A-B, 162A-B) described above. Similarly, the insert can include three or more engagement features at each location on its length, with corresponding features on the inner tray. In other examples, three or more locations on the length of the insert and inner tray can have engagement features, rather than the two locations shown in FIGS. 3A-3C and FIGS. 4A-4C. In other examples where there are engagement features at two or more locations on the length of the insert, a distance between each engagement feature at a first location on the length of the insert or inner tray can vary from a distance between engagement features at a second location on the length in a manner different from that shown in FIG. 4B. In still further examples, a depth of an engagement feature on the inner tray or insert can vary relative to another engagement feature on the inner tray or insert where the depth is measured approximately parallel to a depth of the recessed portion of the inner tray. In the above examples, engagement features can extend from any surface of the insert or inner tray where contact is possible between the two when the insert is placed within the inner tray. Where engagement features are at three or more locations on the length of the insert, the distance between one pair of locations can vary from the distance between another pair of locations.

In still further examples, it is contemplated that the surfaces, including recesses, channels, ridges and various features of the insert and trays can vary in any number of ways as a matter of design choice, with a view to the type of implant envisioned as being stored in the insert. For example, surface features sized to interconnect with corresponding surface features of another insert, i.e., engagement features, can be square in shape. In other examples, the insert includes a generally planar surface with a concave surface recessed from the planar surface to form part of a cavity for storing an implant. A consistent aspect of the design throughout the variants contemplated is that the insert and inner tray both include engagement features that provide for releasable securement of the insert to the inner tray and the movement of the insert relative to the inner tray. Each engagement feature for the above embodiments and examples can be a protrusion or indent, and any combination of protrusions and indents within a single insert or inner tray can be used. Thus, in some examples the insert includes engagement features that are all protrusions, in others, all indents, and still others, a combination of protrusions and indents. It is contemplated that protrusions and indents can be any shape and thus the particular shapes used are a matter of design choice.

In other examples, the depression or cavity within the insert component or the insert can be of any cross-sectional shape, including having varying cross-sectional shape over its length, and it can have any length deemed suitable for a particular implant contemplated for disposal therein. It is envisioned that surface features of the insert can vary in any number of ways provided the insert includes engagement features as described herein and there is a cavity, pocket or other depression in the insert to house an implant. Inserts can be monolithic, such as the insert shown in FIGS. 8A and 8B, or can be an insert assembled from two or more components, such as the two component insert packaging shown in FIGS. 1 and 6. Both monolithic and component-based inserts maintain the sterility of the implant.

In any one of the above embodiments, the insert, inner tray and outer tray can be manufactured from polyethylene terephthalate (PETG). In some examples, a thickness of the insert manufactured from PETG is 0.02 inches while a thickness of the inner and outer trays is 0.03 inches. In other examples, the thickness can be larger or smaller and may depend on the overall size of the package components, the size of the implant, and/or the capability of the equipment used to manufacture the components. In other embodiments, other plastics can be used. In still further embodiments, other materials capable of being formed in the shapes contemplated for the insert and trays can also be used.

Figure 7A:
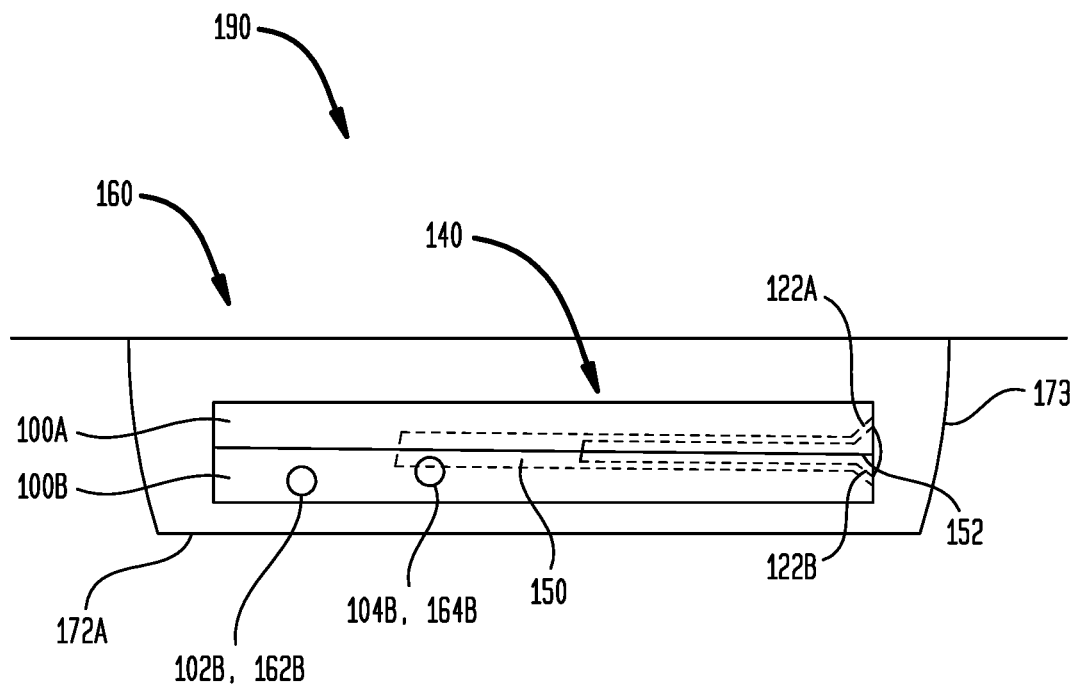
FIGS. 7A-7B are side views of the insert of FIG. 6 disposed in the inner tray of FIGS. 4A-4C, in first and second positions, respectively.
Figure 7B:
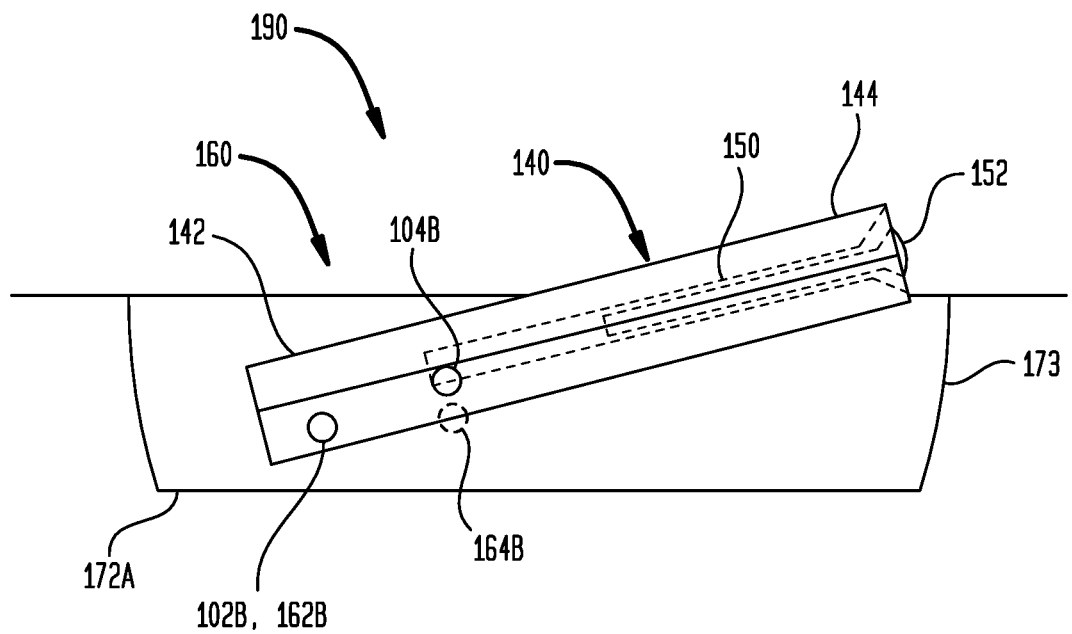

In another aspect, the present invention relates to a method of storing and transporting an implant within a packaging assembly 190 and removing the implant from the insert, all while maintaining the sterility of the implant. In one embodiment, the method begins with insert 140 and inner tray 160 at rest in physically separate locations. An implant 152 is then placed into cavity 150 of insert 140. Implant 152 can be a screw, for example. A cavity 150 (FIGS. 6, 7A and 7B) holds implant 152 in place in at least one direction. For example, where implant 152 is a screw, the head of the screw is held from descending into cavity 150 by tapered channel surfaces 122-A, 122-B (FIG. 7B). Insert 140, with implant 152 disposed therein, is then placed into inner tray 160, as best shown in FIG. 7A. Placement is proper when engagement features 102A-B and 104A-B of lower insert component 100-B of insert 140 correspond to and engage with engagement features 162A-B and 164A-B of inner tray 160 (FIG. 7A). When all engagement features of lower insert component 100-B portion of insert 140 are engaged with engagement features 162B, 164B of inner tray 160, a body of insert 140 is generally in the same plane as, and parallel to, a body of inner tray 160 or bottom surface 172A of inner tray 160. In this manner, implant 152 faces and abuts inner perimeter 173 of inner tray 160, and is held in place as a result. Hereinafter, this will be referred to as a first position of the insert releasably secured to the inner tray. Securement of the insert is releasable because insert 140 can be removed from inner tray 160 by hand. Of course, in a variant, the engagement features can be designed so that removal requires force greater than that possible by a hand of a user, although in such a design the insert would still be releasable. While insert 140 is the first position, implant 152 is inaccessible without first moving insert 140.

A packaging assembly 190 includes insert 140 and inner tray 160, shown releasably secured with one another in FIGS. 7A and 7B. Once packaging assembly 190 is assembled, it is stored for later use or transported to another location, as desired. Because insert 140 is secured to inner tray 160 through the engagement of respective engagement features of the insert and tray, and because implant 152 is held in place within volume 168 of inner tray 160, packaging assembly 190 remains secure and sterile while stored or transported.

When it is desired to remove implant 152 from insert 140, a location on the insert is identified that is opposite an insertion end 144. Such location would be in the vicinity of supplemental protrusions 116A, 116B such as those shown in FIG. 3B for insert component 100, indicated on insert 140 as a pivot end 142. Pressure is applied onto the surface of insert 140 proximal to pivot end 142, and insert 140 moves from the first position, described above, to a second position, as best shown in FIG. 7B. In particular, the pressure applied causes insert 140 to pivot about an axis through engagement features 102A-B and corresponding engagement features 162A-B of inner tray 160 so that insertion end 144 moves further away from bottom surface 172A of inner tray, as shown in FIG. 7B. The manipulation of insert 140 positions it at an angle relative to the inner tray. In one example, the angle between a body of the insert and the bottom surface of the inner tray is between ten and twenty degrees. It is contemplated that the angle can be any angle where an end of implant 152 is visible and accessible from outside of assembly 190 and is not obstructed by inner perimeter 173 or other surfaces of inner tray 160. In this manner, implant 152 is accessible while insert 140 is in the second position. Once in the second position, insert 140 remains there through support provided by engagement with inner tray 160 and without any external support.

Advantages of this method include that an implant is kept sterile when stored or transported within the package and also when the package is moved into the second position to extract the implant. The implant may be stored, transported, and removed from the package, all without contact by a human hand. This is made easier through the stability of the insert in the second position as it holds the implant in place without any external assistance.

Although the method described above references the package shown in FIGS. 1-7B, the method can also be performed utilizing the same steps for implant 252, insert 240 and inner tray 260 shown in FIGS. 8A and 8B. In the first position, engagement features 202A-B and 204A-B are engaged with engagement features 262A-B and 264A-B, respectively. In the second position, engagement features 202A-B are engaged with engagement features 262A-B, but engagement features 204A-B are not engaged with engagement features 264A-B.

The above embodiment can be varied in many ways. For example, the packaging assembly can further include an outer tray where the inner tray is disposed in the outer tray. The inner tray can be placed into the outer tray for additional protection of the inner tray or inner tray and insert structures.

Such placement can occur at any stage of the method, such as prior to placement of the insert into the inner tray or after placement of the insert into the inner tray. In some embodiments, an additional step of extracting the implant from the insert in the second position within the inner tray is performed. This step involves use of a tool to pull the implant from the insert. In other embodiments, the method may commence with insert empty when placed into and secured to inner tray. In other embodiments, the insert of the packaging assembly can be moved back into the first position from the second position. Application of force proximal to the insertion end of the insert will cause the body of insert to once again pivot about the axis through the engagement features proximal to the pivot end of the insert until the insert is in the first position, a position parallel to the body of the inner tray.

In the above and other embodiments, the insert can be removed from the inner tray while the insert is in either the first or second position, regardless of whether or not an implant is disposed in the insert. In any of the above embodiments, the steps described for moving the insert between first and second positions and depositing and removing the insert from the inner tray can be repeated as many times as desired.

In other embodiments, any portion or part of the method steps described for the above embodiments are also contemplated. For example, the method may begin with the insert already engaged with the inner tray in the first or second position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A package comprising:
 a tray including a recessed portion with a bottom surface, the bottom surface including a first engagement feature; and
 an insert sized to fit within the recessed portion of the tray and having a second engagement feature, the insert adapted to support disposal of an implant therein such that the implant is substantially encapsulated by the insert,
 wherein the insert is releasably secured to the tray when the first engagement feature is engaged with the second engagement feature,
 wherein the insert is moveable while releasably secured to the tray such that the implant, when disposed in the insert, is inaccessible when the insert is in a first position and is accessible when the insert is in a second position,
 wherein the implant remains sterile when the implant is inaccessible, and
 wherein a quantity of engagement features engaged with one another in the first position is different than in the second position.

2. The package of claim 1, wherein the first and second engagement features are protrusions or indents.

3. The package of claim 1, wherein the engagement between the second engagement feature of the insert and the first engagement feature of the tray is sufficient to stabilize the insert in the second position.

4. The package of claim 1, further comprising a third engagement feature on the bottom surface of the tray such that the first engagement feature is located at a first location on a length of the tray and the third engagement feature is located at a second location on the length of the tray, the first location different from the second location, and a fourth engagement feature on the insert corresponding to the third engagement feature, wherein the implant, when disposed in the insert, is inaccessible when the third engagement feature is engaged with the fourth engagement feature and is accessible when the third engagement feature is disengaged with the fourth engagement feature.

5. The package of claim 4, wherein the third engagement feature has a shape different than a shape of the first engagement feature.

6. The package of claim 4, wherein the first engagement feature is one of an indent or protrusion and the third engagement feature is the other of the indent or protrusion.

7. The package of claim 4, wherein the third engagement feature is at a first distance from the bottom surface and the first engagement feature is at a second distance from the bottom surface, the first distance different than the second distance.

8. The package of claim 1, further comprising a third engagement feature on the bottom surface of the tray positioned across a longitudinal centerline of the tray opposite the first engagement feature so that a distance of each of the first and third engagement features from the longitudinal centerline of the tray is the same, the third engagement feature corresponding to a fourth engagement feature of the insert.

9. The package of claim 8, wherein the tray further comprises a fifth and a sixth engagement feature separated by a second distance different than the distance between the first and third engagement features of the tray.

10. A package comprising:
a tray including two engagement features; and
an insert including two engagement features corresponding to the two engagement features of the tray so that the insert is engageable with the tray, the insert movable with respect to the tray when engaged thereto,
wherein the two engagement features of the insert, when engaged with the tray, are positioned so that the insert pivots about an axis passing through each of the two engagement features, the insert pivoting about the axis from a first position to a second position,
wherein the insert is adapted to secure an implant therein such that the implant is substantially encapsulated by the insert, the implant inaccessible in the first position and accessible in the second position,
wherein when the implant is inaccessible in the first position the implant is sterile.

11. The package of claim 10, wherein a surface of the insert is parallel to a surface of the tray in the first position and at an angle with respect to the surface of the tray in the second position.

12. The package of claim 10, wherein the implant, when disposed in the insert engaged with the tray in the second position, is coincident with a second axis that only crosses the tray on one side of the insert.

13. The package of claim 12, wherein the second axis is at an angle between 10 degrees and 20 degrees relative to a bottom surface of a recessed portion of the tray.

14. The package of claim 10, wherein the insert includes a cavity shaped to store the implant therein and to hold the implant in place when the insert is in the second position.

* * * * *